(12) United States Patent
McClain

(10) Patent No.: US 8,636,767 B2
(45) Date of Patent: Jan. 28, 2014

(54) SURGICAL SUTURES HAVING INCREASED STRENGTH

(75) Inventor: Jim McClain, Raleigh, NC (US)

(73) Assignee: Micell Technologies, Inc., Raleigh, NC (US)

( * ) Notice: Subject to any disclaimer, the term of this patent is extended or adjusted under 35 U.S.C. 154(b) by 690 days.

(21) Appl. No.: 12/443,959

(22) PCT Filed: Oct. 2, 2007

(86) PCT No.: PCT/US2007/080213
§ 371 (c)(1),
(2), (4) Date: Jul. 8, 2009

(87) PCT Pub. No.: WO2008/042909
PCT Pub. Date: Apr. 10, 2008

(65) Prior Publication Data
US 2010/0030261 A1    Feb. 4, 2010

Related U.S. Application Data

(60) Provisional application No. 60/827,853, filed on Oct. 2, 2006.

(51) Int. Cl.
A61B 17/04 (2006.01)
(52) U.S. Cl.
USPC .......................... 606/230; 606/228
(58) Field of Classification Search
USPC ................................ 606/228–231
See application file for complete search history.

(56) References Cited

U.S. PATENT DOCUMENTS

| 3,087,660 | A | | 4/1963 | Endicott |
| 3,087,860 | A | | 4/1963 | Endicott |
| 3,123,077 | A | * | 3/1964 | Alcamo ................ 606/228 |
| 3,929,992 | A | | 12/1975 | Sehgal et al. |
| 4,326,532 | A | | 4/1982 | Hammar |
| 4,733,665 | A | | 3/1988 | Palmaz |
| 5,158,986 | A | | 10/1992 | Cha et al. |
| 5,243,023 | A | | 9/1993 | Dezern |
| 5,340,614 | A | | 8/1994 | Perman et al. |
| 5,342,621 | A | | 8/1994 | Eury |
| 5,356,433 | A | | 10/1994 | Rowland et al. |
| 5,403,347 | A | | 4/1995 | Roby et al. |
| 5,470,603 | A | | 11/1995 | Staniforth et al. |

(Continued)

FOREIGN PATENT DOCUMENTS

| JP | 2003533492 | 11/2001 |
| WO | WO-2005-042623 A1 | 5/2005 |

(Continued)

OTHER PUBLICATIONS

Latella et al., "Nanoindentation hardness. Young's modulus, and creep behavior of organic-inorganic silica-based sol-gel thin films on copper," J Mater Res 23(9): 2357-2365 (2008).

(Continued)

Primary Examiner — Gregory Anderson
(74) Attorney, Agent, or Firm — Wilson, Sonsini, Goodrich & Rosati

(57) ABSTRACT

The invention relates to increasing the strength of bio-absorbable surgical sutures. The invention allows for delayed bio-absorption of suture materials to allow maintenance of mechanical strength of the suture for example in 'barbed' form.

24 Claims, 1 Drawing Sheet

(56) References Cited

U.S. PATENT DOCUMENTS

| | | | |
|---|---|---|---|
| 5,494,620 A | 2/1996 | Liu et al. | |
| 5,569,463 A | 10/1996 | Helmus et al. | |
| 5,626,611 A * | 5/1997 | Liu et al. | 606/230 |
| 5,811,032 A | 9/1998 | Kawai et al. | |
| 5,824,049 A | 10/1998 | Ragheb et al. | |
| 5,837,313 A | 11/1998 | Ding et al. | |
| 5,873,904 A | 2/1999 | Ragheb et al. | |
| 5,948,020 A | 9/1999 | Yoon et al. | |
| 5,957,975 A | 9/1999 | Lafont et al. | |
| 6,143,037 A | 11/2000 | Goldsten et al. | |
| 6,153,252 A | 11/2000 | Hossainy et al. | |
| 6,190,699 B1 | 2/2001 | Luzzi et al. | |
| 6,273,913 B1 | 8/2001 | Wright et al. | |
| 6,319,541 B1 | 11/2001 | Pletcher et al. | |
| 6,364,903 B2 | 4/2002 | Tseng et al. | |
| 6,368,658 B1 | 4/2002 | Schwartz et al. | |
| 6,372,246 B1 | 4/2002 | Wei et al. | |
| 6,409,716 B1 | 6/2002 | Sahatjian et al. | |
| 6,414,050 B1 | 7/2002 | Howdle et al. | |
| 6,448,315 B1 | 9/2002 | Lidgren et al. | |
| 6,461,644 B1 | 10/2002 | Jackson et al. | |
| 6,497,729 B1 | 12/2002 | Moussy et al. | |
| 6,506,213 B1 | 1/2003 | Mandel et al. | |
| 6,517,860 B1 | 2/2003 | Roser et al. | |
| 6,521,258 B1 | 2/2003 | Mandel et al. | |
| 6,524,698 B1 | 2/2003 | Schmoock | |
| 6,627,246 B2 | 9/2003 | Mehta et al. | |
| 6,649,627 B1 | 11/2003 | Cecchi et al. | |
| 6,660,176 B2 | 12/2003 | Tepper et al. | |
| 6,669,785 B2 | 12/2003 | DeYoung et al. | |
| 6,669,980 B2 | 12/2003 | Hanson et al. | |
| 6,670,407 B2 | 12/2003 | Howdle et al. | |
| 6,706,283 B1 | 3/2004 | Appel et al. | |
| 6,710,059 B1 | 3/2004 | Labrie et al. | |
| 6,720,003 B2 | 4/2004 | Cheng et al. | |
| 6,736,996 B1 | 5/2004 | Carbonell et al. | |
| 6,743,505 B2 * | 6/2004 | Antal et al. | 428/364 |
| 6,749,902 B2 | 6/2004 | Yonker et al. | |
| 6,755,871 B2 | 6/2004 | Damaso et al. | |
| 6,767,558 B2 | 7/2004 | Wang et al. | |
| 6,837,611 B2 | 1/2005 | Kuo et al. | |
| 6,838,089 B1 | 1/2005 | Carlsson et al. | |
| 6,838,528 B2 | 1/2005 | Zhao | |
| 6,860,123 B1 | 3/2005 | Uhlin et al. | |
| 6,884,377 B1 | 4/2005 | Burnham et al. | |
| 6,884,823 B1 | 4/2005 | Plerick et al. | |
| 6,897,205 B2 | 5/2005 | Beckert et al. | |
| 6,905,555 B2 | 6/2005 | DeYoung et al. | |
| 6,939,569 B1 | 9/2005 | Green et al. | |
| 7,163,715 B1 | 1/2007 | Kramer | |
| 7,201,940 B1 | 4/2007 | Kramer | |
| 7,279,174 B2 | 10/2007 | Pacetti et al. | |
| 7,378,105 B2 | 5/2008 | Burke et al. | |
| 7,455,658 B2 | 11/2008 | Furst et al. | |
| 2001/0049551 A1 | 12/2001 | Tseng et al. | |
| 2002/0091433 A1 | 7/2002 | Ding et al. | |
| 2002/0133072 A1 | 9/2002 | Wang et al. | |
| 2003/0031699 A1 | 2/2003 | Van Antwerp | |
| 2003/0088307 A1 | 5/2003 | Shulze et al. | |
| 2003/0125800 A1 | 7/2003 | Shulze et al. | |
| 2003/0143315 A1 | 7/2003 | Pui et al. | |
| 2003/0180376 A1 | 9/2003 | Dalal et al. | |
| 2003/0185964 A1 | 10/2003 | Weber et al. | |
| 2003/0204238 A1 | 10/2003 | Tedeschi | |
| 2003/0222017 A1 | 12/2003 | Fulton et al. | |
| 2004/0106982 A1 | 6/2004 | Jalisi | |
| 2004/0126542 A1 | 7/2004 | Fujiwara et al. | |
| 2004/0193177 A1 | 9/2004 | Houghton et al. | |
| 2004/0193262 A1 | 9/2004 | Shadduck | |
| 2004/0236416 A1 | 11/2004 | Falotico | |
| 2005/0003074 A1 | 1/2005 | Brown et al. | |
| 2005/0004661 A1 | 1/2005 | Lewis et al. | |
| 2005/0010275 A1 | 1/2005 | Sahatjian et al. | |
| 2005/0015046 A1 | 1/2005 | Weber et al. | |
| 2005/0019747 A1 | 1/2005 | Anderson et al. | |
| 2005/0049694 A1 | 3/2005 | Neary | |
| 2005/0069630 A1 | 3/2005 | Fox et al. | |
| 2005/0079274 A1 | 4/2005 | Palasis et al. | |
| 2005/0147734 A1 | 7/2005 | Seppala et al. | |
| 2005/0175772 A1 | 8/2005 | Worsham et al. | |
| 2005/0177223 A1 | 8/2005 | Palmaz | |
| 2005/0191491 A1 | 9/2005 | Wang et al. | |
| 2005/0196424 A1 | 9/2005 | Chappa | |
| 2005/0216075 A1 | 9/2005 | Wang et al. | |
| 2005/0238829 A1 | 10/2005 | Motherwell et al. | |
| 2005/0288481 A1 | 12/2005 | Desnoyer et al. | |
| 2006/0020325 A1 | 1/2006 | Burgermeister et al. | |
| 2006/0094744 A1 | 5/2006 | Maryanoff et al. | |
| 2006/0121089 A1 | 6/2006 | Michal et al. | |
| 2006/0134211 A1 | 6/2006 | Lien et al. | |
| 2006/0136041 A1 | 6/2006 | Schmid et al. | |
| 2006/0188547 A1 | 8/2006 | Bezwada | |
| 2006/0193886 A1 | 8/2006 | Owens et al. | |
| 2006/0193890 A1 | 8/2006 | Owens | |
| 2006/0198868 A1 | 9/2006 | Dewitt et al. | |
| 2006/0222756 A1 | 10/2006 | Davila et al. | |
| 2006/0276877 A1 | 12/2006 | Owens et al. | |
| 2007/0009564 A1 | 1/2007 | McClain et al. | |
| 2007/0059350 A1 | 3/2007 | Kennedy et al. | |
| 2007/0123977 A1 | 5/2007 | Cottone et al. | |
| 2007/0196423 A1 | 8/2007 | Ruane et al. | |
| 2007/0203569 A1 | 8/2007 | Burgermeister et al. | |
| 2007/0259017 A1 | 11/2007 | Francis | |
| 2008/0051866 A1 * | 2/2008 | Chen et al. | 623/1.11 |
| 2008/0075753 A1 | 3/2008 | Chappa | |
| 2008/0118543 A1 | 5/2008 | Pacetti et al. | |
| 2008/0206304 A1 | 8/2008 | Lindquist et al. | |
| 2008/0213464 A1 | 9/2008 | O'Connor | |
| 2008/0255510 A1 | 10/2008 | Wang | |
| 2008/0292776 A1 | 11/2008 | Dias et al. | |
| 2008/0300669 A1 | 12/2008 | Hossainy | |
| 2009/0062909 A1 | 3/2009 | Taylor et al. | |
| 2009/0105809 A1 | 4/2009 | Lee et al. | |
| 2009/0292351 A1 | 11/2009 | McClain et al. | |

FOREIGN PATENT DOCUMENTS

| | | |
|---|---|---|
| WO | WO-2005-117942 A2 | 12/2005 |
| WO | WO-2006-083796 A2 | 8/2006 |
| WO | WO-2006-099276 A2 | 9/2006 |
| WO | WO-2007-011707 A2 | 1/2007 |
| WO | WO-2007-011707 A3 | 1/2007 |
| WO | WO-2007-011708 A2 | 1/2007 |
| WO | WO-2007-011708 A3 | 1/2007 |
| WO | WO-2007-127363 A2 | 1/2007 |
| WO | WO-2008-046641 A2 | 4/2008 |
| WO | WO-2008-046642 A2 | 4/2008 |
| WO | WO 2008/086369 | 7/2008 |
| WO | WO-2008-131131 A1 | 10/2008 |
| WO | WO 2010/009335 | 1/2010 |
| WO | WO-2010-111196 A2 | 9/2010 |
| WO | WO-2010-111196 A3 | 9/2010 |
| WO | WO-2010-111232 A3 | 9/2010 |
| WO | WO-2010-111232 A9 | 9/2010 |
| WO | WO-2010-111238 A2 | 9/2010 |
| WO | WO-2010-111238 A3 | 9/2010 |
| WO | WO-2010-120552 A2 | 10/2010 |
| WO | WO-2010-120552 A3 | 10/2010 |
| WO | WO-2010-121187 A2 | 10/2010 |
| WO | WO-2010-121187 A3 | 10/2010 |
| WO | WO-2011-009096 A1 | 1/2011 |

OTHER PUBLICATIONS

Schmidt et al., "A Comparison of the Mechanical Performance Characteristics of Seven Drug-Eluting Stent Systems," Catheterization and Cardiovascular Interventions 73:350-360 (2009).

Schmidt et al., "Trackability, Crossability, and Pushability of Coronary Stent Systems—An Experimental Approach," Biomed Techn 47 (2002), Erg. 1, S. 124-126.

Schmidt et al., "In vitro measurement of quality parameters of stent-catheter systems," Biomed Techn 50(S1):1505-1506 (2005).

Schmidt et al., "New aspects of in vitro testing of arterial stents based

(56) References Cited

OTHER PUBLICATIONS on the new European standard," EN 14299, [online] (2009), [retrieved on Mar. 10, 2001] http://www.lib0ev.de/pl/pdf/EN14299.pdf (2009).
Szabadits et al., "Flexibility and trackability of laser cut coronary stent systems," Acta of Bioengineering and Biomechanics 11(3):11-18 (2009).
PCT/US10/42355 Search Report mailed Sep. 2, 2010.
PCT/US10/28253 Search Report and Written Opinion mailed Dec. 6, 2010.
PCT/US10/28265 Search Report and Written Opinion mailed Dec. 13, 2010.
PCT/US10/28195 Search Report and Written Opinion mailed Jan. 21, 2011.
PCT/US10/31470 Search Report and Written Opinion mailed Jan. 28, 2011.
PCT/US10/29494 Search Report and Written Opinion mailed Feb. 7, 2011.
PCT/US11/22623 Search Report and Written Opinion mailed Mar. 28, 2011.
U.S. Appl. No. 12/426,198 Office Action Mailed Mar. 23, 2011.
U.S. Appl. No. 11/995,685 Office Action Mailed Aug. 20, 2010.
U.S. Appl. No. 11/995,685 Office Action Mailed Nov. 24, 2009.
U.S. Appl. No. 11/158,724 Office Action Mailed Sep. 8, 2008.
U.S. Appl. No. 11/158,724 Office Action Mailed Sep. 17, 2009.
Domingo, C. et al., "Precipication of ultrafine organic crystals from the rapid expansion of supercritical solutions over a capillary and a frit nozzle," J. Supercritical Fluids 10:39-55 (1997).
Mario, C.D. et al., "Drug-Eluting Bioabsorbable Magnesium Stent," J. Interventional Cardiology 16(6):391-395 (2004).
McAlpine, J.B. et al., "Revised NMR Assignments for Rapamycine," J. Antibiotics 44:688-690 (1991).
Ong and Serruys, "Technology Insight: an overview of research in drug-eluting stents," Nat. Clin. Parct. Cardiovas. Med. 2(12):647-658 (2005).
PCT/US06/24221 Search Report mailed Jan. 29, 2007.
PCT/US06/27321 Search Report mailed Oct. 16, 2007.
PCT/US06/27322 Search Report mailed Apr. 25, 2007.
PCT/US07/10227 Search Report mailed Aug. 8, 2008.
PCT/US07/82275 Search Report mailed Apr. 18, 2008.
PCT/US07/080213 Search Report dated Apr. 16, 2008.
PCT/US08/11852 Search Report dated Dec. 19, 2008.
PCT/US08/50536 Search Report dated Jun. 2, 2008.
PCT/US08/60671 Search Report dated Sep. 5, 2008.
PCT/US08/64732 Search Report dated Sep. 4, 2008.
PCT/US09/41045 Search Report dated Aug. 11, 2009.
Schreiber, S.L. et al., "Atomic Structure of the Rapamycin Human Immunophilin FKBP-12 Complex," J. Am. Chem. Soc. 113:7433-7435 (1991).
PCT/US09/50883 Search Report dated Nov. 17, 2009.
Serruys, Patrick et al., Comparison of Coronary-Artery Bypass Surgery and Stenting for the Treatment of Multivessel Disease, N. Engl. J. Med., 2001, vol. 344, No. 15, pp. 1117-1124.
PCT/US2011/032371, International Search Report dated Jul. 7, 2011.

\* cited by examiner

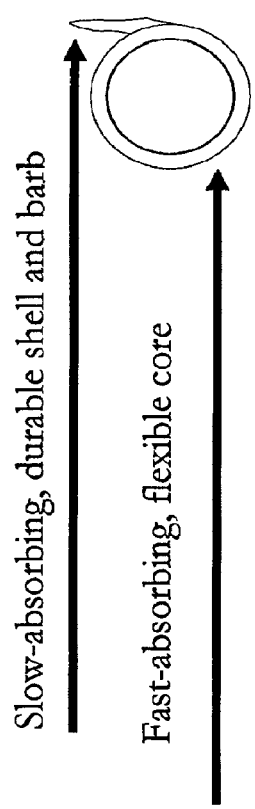

SURGICAL SUTURES HAVING INCREASED STRENGTH

RELATED APPLICATIONS

The present application claims priority to U.S. Provisional Application No. 60/827,853, filed on Oct. 2, 2006; the contents of which are incorporated herein by reference in their entirety.

FIELD OF THE INVENTION

The present invention relates to methods for forming a suture with delayed bioabsorption and sutures made thereby.

BACKGROUND OF THE INVENTION

Bioabsorbable surgical devices such as, for example, sutures, made from copolymers derived from one or more of glycolide, lactide, p-dioxanone, epsilon-caprolactone and/or trimethylene carbonate are known in the art. However, filaments prepared from certain such copolymers are not dimensionally stable and require a freezing step to maintain a desired physical dimension. See, e.g. U.S. Pat. No. 5,494,620 which discloses the details of and benefits derived from a freezing operation. U.S. Pat. No. 5,403,347 discloses a block copolymer wherein one of the blocks is made from hard phase forming monomers (preferably glycolide) and another of the blocks is made from soft phase forming monomers (e.g., p-dioxanone) copolymerized with randomly intermingled units of other soft phase forming monomers (e.g., trimethylene carbonate)

A surgical suture is either a synthetic monofilament or a braided multifilament structure or alternatively a cut, ground or polished ligature derived from animal intestines, used for tissue approximation or the attachment of an implantable device. Sutures can be made of either resorbable or non-resorbable materials. Resorbable sutures degrade and disintegrate inside the body after exposure to the in-vivo environment in a pre-determined time interval, so there is no need for a second surgery to remove the suture after the tissue is healed at the site of the wound. On the other hand the non-resorbable sutures do not degrade, so there is a need to remove them after healing of the wound, unless they are being used as a permanent implant.

Surgical suture material usable for wound closure comprises non-absorbable and absorbable materials. Absorbable surgical sewing threads based on natural biological materials, particularly cat gut and absorbable synthetic threads are known. Absorbable synthetic suture material can inter alia be produced from polyglycolic acid (PGA). In the physiological environment the sewing threads undergo a hydrolysis. The 50% breaking strength loss, also known as the half-life period, serves as a measure for the hydrolytic decomposition of the polymer material. Surgical sewing threads formed from braided PGA multifilaments (e.g. obtainable under the trademark DEXON) within 21 days have a 50% breaking strength loss and an absorption of hydrolyzates within 100 to 120 days. A multifilament sewing thread produced from a glycolide-lactide copolymer with a comonomer ratio of 90:10 has similar characteristics (obtainable under the trademark VICRYL). In vivo, after 25 days it loses 50% of its initial strength and is absorbed after more than 80 days.

What is needed is bioabsorbale sutures with improved strength having increased 50% breaking strength.

SUMMARY OF THE INVENTION

One aspect of the invention relates to increasing the strength of bio-absorbable surgical sutures. The invention allows for delayed bioabsorption of suture materials to allow maintenance of mechanical strength of the suture for example in 'barbed' form.

In particular, the invention allows for maintaining the mechanical attributes of the 'barb' (a 'barb' being characterized as a small protrusion from the filament that is prone to facile hydrolysis and/or degradation).

In one aspect of the invention, crystalline domains are formed on the surface of a barbed suture via exposure to supercritical fluid(s) (SCF) over a controlled temperature profile where solvent-induced crystallization can be achieved with the SCF. Employing scf solvents provides increased polymer crystallization without the legacy of solvent residue or severe drying conditions.

In one embodiment of the invention, a bioabsorbable suture is processed, through a profile of temperature-pressure-time such that the crystallinity at the surface is increased, thus inhibiting the bioabsorption of the mechanically critical surface features in a barbed suture.

Another aspect of the invention provides co-filament (core-shell) suture with barb structure being formed only in the harder and slower to absorb outer shell polymer.

The invention provides a co-filament suture material such that the outer 'sheaf' consists of a much slower absorbing material (e.g., poly($\epsilon$-caprolactone), etc.) such that the barbs can be cut solely into this harder material. Bioabsorption would initially be slow, maintaining mechanical strength of the barbs, followed by full absorption of the suture.

In yet a further embodiment, the invention provides a method of forming absorbable, biocompatible suture filament, comprising the steps of: forming a suture comprising a bio-absorbable polymer; and inserting a chemical entity into the polymer to inhibit ester hydrolysis, thereby slowing down bioabsorption and loss of mechanical strength.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 shows a suture according to one embodiment of the invention wherein the suture comprises a core formed by a fast absorbing material and a shell formed by a slow absorbing material, and a barb structure formed in the shell.

DETAILED DESCRIPTION OF THE INVENTION

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations and variations thereof.

One aspect of the invention relates to increasing the strength of bio-absorbable surgical sutures. The invention allows for delayed bioabsorption of suture materials to allow maintenance of mechanical strength of the suture for example in 'barbed' form.

In particular, the invention allows for maintaining the mechanical attributes of the 'barb' (a 'barb' being characterized as a small protrusion from the filament that is prone to facile hydrolysis and/or degradation).

In one aspect of the invention, crystalline domains are formed on the surface of a barbed suture via exposure to supercritical fluid(s) over a controlled temperature profile where solvent-induced crystallization can be achieved with the SCF. Employing scf solvents provides increased polymer crystallization without the legacy of solvent residue or severe drying conditions.

In one embodiment of the invention, a bioabsorbable suture is processed, through a profile of temperature-pressure-time such that the crystallinity at the surface is increased, thus inhibiting the bioabsorption of the mechanically critical surface features in a barbed suture. In one embodiment, the suture is immersed into a supercritical fluid at a temperature greater than the glass transition temperature (Tg) of the material that forms the suture, yet lower than the melting temperature (e.g. Tg<Tprocess<Tm). The suture is then quenched by reducing the temperature of the suture to below the Tg of the suture material (e.g. via venting the sc). The Tg of polymers that form the suture is depressed in the presence of a compressed gas or supercritical fluid Another aspect of the invention provides co-filament (core-shell) suture with barb structure being formed only in the harder and slower to absorb outer shell polymer.

The invention provides a co-filament suture material such that the outer 'sheaf' consists of a much slower absorbing material (e.g., poly($\epsilon$-caprolactone), etc.) such that the barbs can be cut solely into this harder material. Bioabsorption would initially be slow, maintaining mechanical strength of the barbs, followed by full absorption of the suture.

The method of the invention allows for a 5-30% decrease in absorption rate.

In another aspect, the invention provides a suture with a strengthened structure by inserting a chemical adjunct (GRAS) into the polymer to inhibit ester hydrolysis, therefore slowing down bioabsorption and loss of mechanical strength.

In one embodiment, the invention provides a process of forming a suture having increased strength, the process comprising treating the suture with a supercritical fluid.

The treatment comprises increasing crystallinity of the suture.

In one embodiment, the increased crytsallinity is located on the surface of the suture.

The absorbable material may comprise an abosorbable polymer.

A suture produced by the process of the invention provides numerous advantages. For example, absorbability of the suture can be decreased to 5 to 30% of the absorbability of a suture which is not treated with a supercritical fluid.

Preferred sutures comprise a barb structure, wherein the strength of the barb structure is improved by treating the suture with the supercritical fluid.

In another aspect, the invention provides an absorbable suture comprising: a core comprising a fast absorbing material; and a shell covering the core, wherein the shell comprises a slow-absorbing material. Preferably, the shell comprises a barb structure.

The suture of the invention has greater mechanical strength. The invention provides sutures wherein the fast absorbing core material is selected from DLPLA—poly(dl-lactide); LPLA—poly(l-lactide); PGA—polyglycolide; PDO—poly(dioxanone); PGA-TMC—poly(glycolide-co-trimethylene carbonate); PGA-LPLA—poly(l-lactide-co-glycolide); PGA-DLPLA—poly(dl-lactide-co-glycolide); LPLA-DLPLA—poly(l-lactide-co-dl-lactide); PDO-PGA-TMC—poly(glycolide-co-trimethylene carbonate-co-dioxanone).

In one embodiment, the core and shell materials are co-extruded. In another embodiment, the core is coated with the slow absorbing material to form the shell.

In yet another aspect, the invention provides a method of forming absorbable, biocompatible suture filament, comprising the steps of: forming a fast absorbing a core; and forming a slow-absorbing shell covering the core.

In one embodiment, the core and shell are formed by co-extruding a fast absorbing polymer and a slow-absorbing polymer.

In another embodiment, forming the shell comprises coating the core with a slow absorbing material.

In one embodiment, the method of the invention further comprises treating the coating with a supercritical fluid.

In yet a further embodiment, the invention provides a method of forming absorbable, biocompatible suture filament, comprising the steps of: forming a suture comprising a bio-absorbable polymer; and inserting a chemical entity into the polymer to inhibit ester hydrolysis, thereby slowing down bioabsorption and loss of mechanical strength.

DEFINITIONS

As used in the present specification, the following words and phrases are generally intended to have the meanings as set forth below, except to the extent that the context in which they are used indicates otherwise.

"Pharmaceutical agent" as used herein refers to any of a variety of drugs or pharmaceutical compounds that can be used as active agents to prevent or treat a disease (meaning any treatment of a disease in a mammal, including preventing the disease, i.e. causing the clinical symptoms of the disease not to develop; inhibiting the disease, i.e. arresting the development of clinical symptoms; and/or relieving the disease, i.e. causing the regression of clinical symptoms). It is possible that the pharmaceutical agents of the invention may also comprise two or more drugs or pharmaceutical compounds.

"Polymer" as used herein, refers to a series of repeating monomeric units that have been cross-linked or polymerized. Any suitable polymer can be used to carry out the present invention. It is possible that the polymers of the invention may also comprise two, three, four or more different polymers. In some embodiments, of the invention only one polymer is used. In some preferred embodiments a combination of two polymers are used. Combinations of polymers can be in varying ratios, to provide coatings with differing properties. Those of skill in the art of polymer chemistry will be familiar with the different properties of polymeric compounds.

"Stabilizing agent" as used herein refers to any substance that maintains or enhances the stability of the suture. Ideally these stabilizing agents are classified as Generally Regarded As Safe (GRAS) materials by the US Food and Drug Administration (FDA). The stabilizing agent is incorporated in the material of the suture to reduce or inhibit bioabsorption (e.g., of a bioabsorbable polymer). Examples of stabilizing agents include, but are not limited to a bronsted or lowery base, preferably an organic base such as an amine-containing molecule.

"Compressed fluid" as used herein refers to a fluid of appreciable density (e.g., >0.2 g/cc) that is a gas at standard temperature and pressure. "Supercritical fluid", "near-critical fluid", "near-supercritical fluid", "critical fluid", "densified fluid" or "densified gas" as used herein refers to a compressed fluid under conditions wherein the temperature is at least 80% of the critical temperature of the fluid and the pressure is at least 50% of the critical pressure of the fluid.

Examples of substances that demonstrate supercritical or near critical behavior suitable for the present invention include, but are not limited to carbon dioxide, isobutylene, ammonia, water, methanol, ethanol, ethane, propane, butane, pentane, dimethyl ether, xenon, sulfur hexafluoride, halogenated and partially halogenated materials such as chlorofluorocarbons, hydrochlorofluorocarbons, hydrofluorocarbons, perfluorocarbons (such as perfluoromethane and perfuoropropane, chloroform, trichloro-fluoromethane, dichloro-difluoromethane, dichloro-tetrafluoroethane) and mixtures thereof.

"scf-processing" as used herein refers to the process by which parts of the matrix or the entire polymer matrix is exposed to supercritical fluid. In one aspect, scf-processing is employed to generate crystalline domains in a suture, or the shell of the suture, thereby increasing the strength of the suture or the outer shell of the suture. In other embodiments scf-processing allows the formation of a continuous shell deposited on a core of a suture. The scf-process is controlled to produce a fully conformal continuous matrix. In this latter embodiment, scf-processing also allows for strengthening the outer shell of the suture through increased crystallization.

What is claimed is:

1. An absorbable suture comprising:
a core comprising a fast absorbing polymer;
a shell covering said core, wherein said shell comprises a stronger, more durable or slow-absorbing polymer,
wherein said shell comprises a chemical entity that inhibits ester hydrolysis, thereby slowing down bioabsorption and loss of mechanical strength, and wherein said chemical entity is a base.

2. The suture of claim 1, wherein said shell comprises a barb structure.

3. The suture of claim 2, wherein the strength of said barb structure is improved by treating with a supercritical fluid as compared to the strength of a non-treated barb structure.

4. The suture of claim 2, wherein the rate of absorption of said barb structure is decreased by treating with a supercritical fluid as compared to the rate of absorption of a non-treated barb structure.

5. The suture of claim 1, wherein said suture undergoes 50% breaking strength loss in greater than 21 days, and is absorbed in greater than 120 days.

6. The suture of claim 1 wherein said fast absorbing polymer is selected from DLPLA—poly(dl-lactide); LPLA—poly(l-lactide); PGA—polyglycolide; PDO—poly(dioxanone); PGA-TMC—poly(glycolide-co-trimethylene carbonate); PGA-LPLA—poly(l-lactide-co-glycolide); PGA-DLPLA—poly(dl-lactide-co-glycolide); LPLA-DL-PLA—poly(l-lactide-co-dl-lactide); PDO-PGA-TMC—poly(glycolide-co-trimethylene carbonate-co-dioxanone.

7. The suture of claim 1, wherein said slow absorbing polymer is poly(ε-caprolactone).

8. The suture of claim 1 wherein said core and shell materials are co-extruded.

9. The suture of claim 1 wherein said core is coated with said slow absorbing material to form said shell.

10. The suture of claim 1, wherein the suture is treated with a supercritical fluid (SCF).

11. The suture of claim 10, wherein said treating comprises immersing said suture into a supercritical fluid at a temperature greater than the glass transition temperature (Tg) of the material that forms the shell, yet lower than the melting temperature of said material.

12. The suture of claim 10, wherein crystallinity in said suture is increased following treating with the supercritical fluid (SCF) as compared to the crystallinity of a non-treated suture.

13. The suture of claim 10, wherein the suture comprises a crystalline domain on a surface of said suture.

14. The suture of claim 13, wherein said shell comprises a barb structure and wherein the crystalline domain is on a surface of said barb.

15. The suture of claim 10, wherein the crystallinity on a surface of the suture is greater than crystallinity of a non-surface of the suture.

16. The suture of claim 10, wherein absorbability of said suture is 5% to 30% of the absorbability of a suture which is not treated with a supercritical fluid.

17. The suture of claim 1, wherein the Tg of said shell is depressed in the presence of a compressed gas or supercritical fluid.

18. The suture of claim 1 further comprising a pharmaceutical agent.

19. The suture of claim 1, wherein said base is a bronsted or lowery base.

20. The suture of claim 1, wherein said base comprises an organic base.

21. The suture of claim 20, wherein said organic base comprises an amine-containing molecule.

22. The suture of claim 1, wherein the suture is without solvent residue despite employing a solvent in forming the suture.

23. The suture of claim 1, wherein the suture comprises solvent-induced polymer crystallinity without solvent residue.

24. The suture of claim 1, wherein the suture comprises solvent-induced polymer crystallinity without reaching or exceeding the melting temperature of the shell material.

* * * * *

UNITED STATES PATENT AND TRADEMARK OFFICE
CERTIFICATE OF CORRECTION

PATENT NO.         : 8,636,767 B2
APPLICATION NO.    : 12/443959
DATED              : January 28, 2014
INVENTOR(S)        : Jim McClain It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 904 days.

Signed and Sealed this

Twenty-second Day of September, 2015

Michelle K. Lee
*Director of the United States Patent and Trademark Office*